United States Patent [19]

Johnson, Jr. et al.

[11] Patent Number: 4,916,076
[45] Date of Patent: Apr. 10, 1990

[54] METHOD TO PREDICT RELATIVE HYDRIDING WITHIN A GROUP OF ZIRCONIUM ALLOYS UNDER NUCLEAR IRRADIATION

[75] Inventors: A. Burtron Johnson, Jr., Richland; Ira S. Levy, Kennewick; Dennis J. Trimble, Kennewick; Donald D. Lanning, Kennewick; Franna S. Gerber, Richland, all of Wash.

[73] Assignee: Battelle Memorial Institute, Richland, Wash. ; a part interest

[21] Appl. No.: 208,332

[22] Filed: Jun. 17, 1988

[51] Int. Cl.⁴ .................... G01N 31/00; G21C 17/00
[52] U.S. Cl. ......................... 436/6; 73/865.6; 376/245
[58] Field of Search .............. 376/308, 463, 245; 73/61.2, 865.6; 422/11, 53; 436/6

[56] References Cited

U.S. PATENT DOCUMENTS 3,909,370  9/1975  Videm et al. ............... 376/416
4,440,862  4/1984  Cheng et al. ............... 73/61.2
4,451,445  5/1984  Cheng et al. ............... 420/900

OTHER PUBLICATIONS

Kass, "Corrosion and Hydrogen Pickup of Zircaloy in Concentrated Lithium Hydroxide Solutions", Clearinghouse for Fed. Sci. and Tech. Inf., Nat. Bur. Stand., Cat. #WAPD-TM-656, 52 pages (Oct. 1967).
Murgatroyd et al., "Hydriding Zircaloy-2 in Lithium Hydroxide Solutions", J. Nuclear Mat. 23:249≧256 (1967).
Van Nostrand's Sci. Encyclopedia, 5th Ed., p. 2367 (1976).

Primary Examiner—Daniel Wasil
Attorney, Agent, or Firm—Klarquist, Sparkman, Campbell, Leigh & Whinston

[57] ABSTRACT

An out-of-reactor method for screening to predict relative in-reactor hydriding behavior of zirconium-based materials is disclosed. Samples of zirconium-based materials having different composition and/or fabrication are autoclaved in a relatively concentrated (0.3 to 1.0M) aqueous lithium hydroxide solution at constant temperatures within the water reactor coolant temperature range (280° to 316° C.). Samples tested by this out-of-reactor procedure, when compared on the basis of the ratio of hydrogen weight gain to oxide weight gain, accurately predict the relative rate of hyriding for the same materials when subject to in-reactor (irradiated) corrision.

7 Claims, 1 Drawing Sheet

TEST 7 - HYDROGEN vs OXYGEN WEIGHT GAINS 4,916,076

METHOD TO PREDICT RELATIVE HYDRIDING WITHIN A GROUP OF ZIRCONIUM ALLOYS UNDER NUCLEAR IRRADIATION

This invention was made with government support under Contract No. DE-ACO6-76RLO 1830 awarded by the U.S. Department of Energy. The government has certain rights in this invention.

BACKGROUND OF THE INVENTION

This invention concerns a method for predicting the relative hydriding within a group of zirconium materials under nuclear irradiation. More specifically, it concerns a method for testing samples of zirconium materials outside of a nuclear reactor to determine their relative hydriding efficiencies under irradiation.

Zirconium metal alloys are widely used in core components and structures of water cooled nuclear fission reactors because of their low neutron cross section, among other apt properties for such service. Note for instance U.S. Pat. No. 4,212,686. Several zirconium alloy compositions have been developed and marketed primarily for nuclear reactor applications. Typical of such alloy compositions of zirconium are the commercially available materials identified as Zircaloy-2 and Zircaloy-4, comprising alloys set forth in U.S. Pat. Nos. 2,772,964 and 3,148,055. A niobium containing alloy of zirconium for reactor service is disclosed in U.S. Pat. Nos. 3,150,972 and 4,212,686.

The Zircaloys comprise alloy compositions containing at least about 95 percent by weight of zirconium metal and including in percent by weight up to about 2.0 percent of tin, up to about 0.5 percent of iron, up to about 0.5 percent of chromium and 0 to about 0.15 percent of nickel.

It is a problem that zirconium alloy materials absorb hydrogen generated by a corrosion reaction which occur under irradiation. The absorption of hydrogen causes embrittlement of the metal which is believed to be one of the most important factors limiting the life of zirconium alloys in pressurized water reactors. 5

Variations in the hydriding properties of light water reactor (LWR) cladding materials and other zirconium-based components are thus a concern in predicting the behavior of such materials in reactor service. Hydriding propensities sometimes vary substantially among materials that meet the specifications for a given alloy system. While lot-to-lot variations are not unique to zirconium-based systems, they have resulted in hydriding rates that vary by an order of magnitude for Zircaloy-2 materials in the same reactor environments [Johnson et al., *Radiation Enhanced Oxidation of Zircaloy-2 in pH/10/LiOH and pH 10 NH₄OH*, BNWL-463, Battelle Pacific Northwest Laboratory, Richland, Wash. (1967); Johnson, *Zirconium Alloy Oxidation and Hydriding Under Irradiation: Review of Pacific Northwest Laboratory's Test Program Results*, CPRI NP-5132, Electric Power Research Institute, Palo Alto, Calif. (1987), Lanning et al., "Waterside Corrosion Hydrogen Pickup, and Hydrogen Redistribution in Zircaloy-2 Pressure Tubes During Long Exposure in N Reactor", *Third International Symposium on Environmental Degradation of Materials in Nuclear Power Systems - Water Reactors*, Aug. 30–Sept. 3, 1987, Traverse City, Mich.].

The fabrication and compositional variables that account for lot-to-lot differences are only partially understood. For example, elimination of nickel has been regarded as a key factor to improve Zircaloy hydriding resistance. However, Cheng et al. [*International Symposium in Nuclear Power Systems - Water Reactors*, p. 274, NACE/AIME/ANS, Myrtle Beach, S.C. (1984)] propose that fabrication plays a role in the hydriding property differences of Zircaloy-2 and Zircaloy-4.

Kass et al. demonstrated that increasing silicon content improves Zircaloy-2 resistance to out-of-reactor hydriding [*Effects of Silicon, Nitrogen, and Oxygen on the Corrosion and Hydrogen Absorption Performance of Zircaloy-2*, WAPD-283, Bettis Atomic Power Laboratory, Pittsburgh, Pa. (1963)], but provided no basis to judge the efficacy of silicon to suppress hydriding of Zircaloy-2 under irradiation.

U.S. Pat. No. 4,440,862 (Cheng et al.) describes an out-of-reactor procedure for testing zirconium alloys. But, that test concerns nodular corrosion and is in no way useful to predict hydriding characteristics [Johnson et al. (1967); Johnson (1987)].

Thus, there remains a need for an out-of-reactor test to predict zirconium alloy hydriding during reactor service. Such a test could be used in cladding fabrication to discriminate hydriding characteristics of various lots of currently used alloys and in research for optimization of alloys with respect to hydriding. Such optimization is needed since the trend to higher fuel burnups is resulting in cladding hydrogen contents above 500 ppm and associated loss of ductility [Pyecha et al., "Waterside Corrosion of PWR Fuel Rods through Burnups of 50,000 MWd/MTU", *ANS Topical Meeting on LWR Fuel Performance*, Apr. 21–24, 1985, Orlando, Fla.].

SUMMARY OF THE INVENTION

The present invention is an out-of-reactor method that successfully predicts, in a reasonable amount of time, the in-reactor hydriding ranking for zirconium-based materials.

Samples of zirconium-based materials to be compared are placed in an autoclave containing concentrated LiOH solution at an elevated temperature to charge hydrogen into the samples. By regulating conditions in the autoclave to maintain a weight gain rate of about 1.5 to 15 mg/dm² per day (mdd), preferably less than about 6 mdd, hydriding rankings for materials of the test samples are the same as rankings for like materials used in reactor service.

It is an object of this invention to provide means for determining the relative resistance to hydriding for alloys of zirconium.

It is a specific object of this invention to discriminate hydriding susceptibility of zirconium alloys for their use in water cooled, nuclear fission reactor services.

It is also an object of this invention to provide means for determining which variables (compositional and/or fabrication) control hydriding of zirconium alloy materials and how such variables should be regulated to provide hydriding-resistant materials.

DETAILED DESCRIPTION

Figure 1:
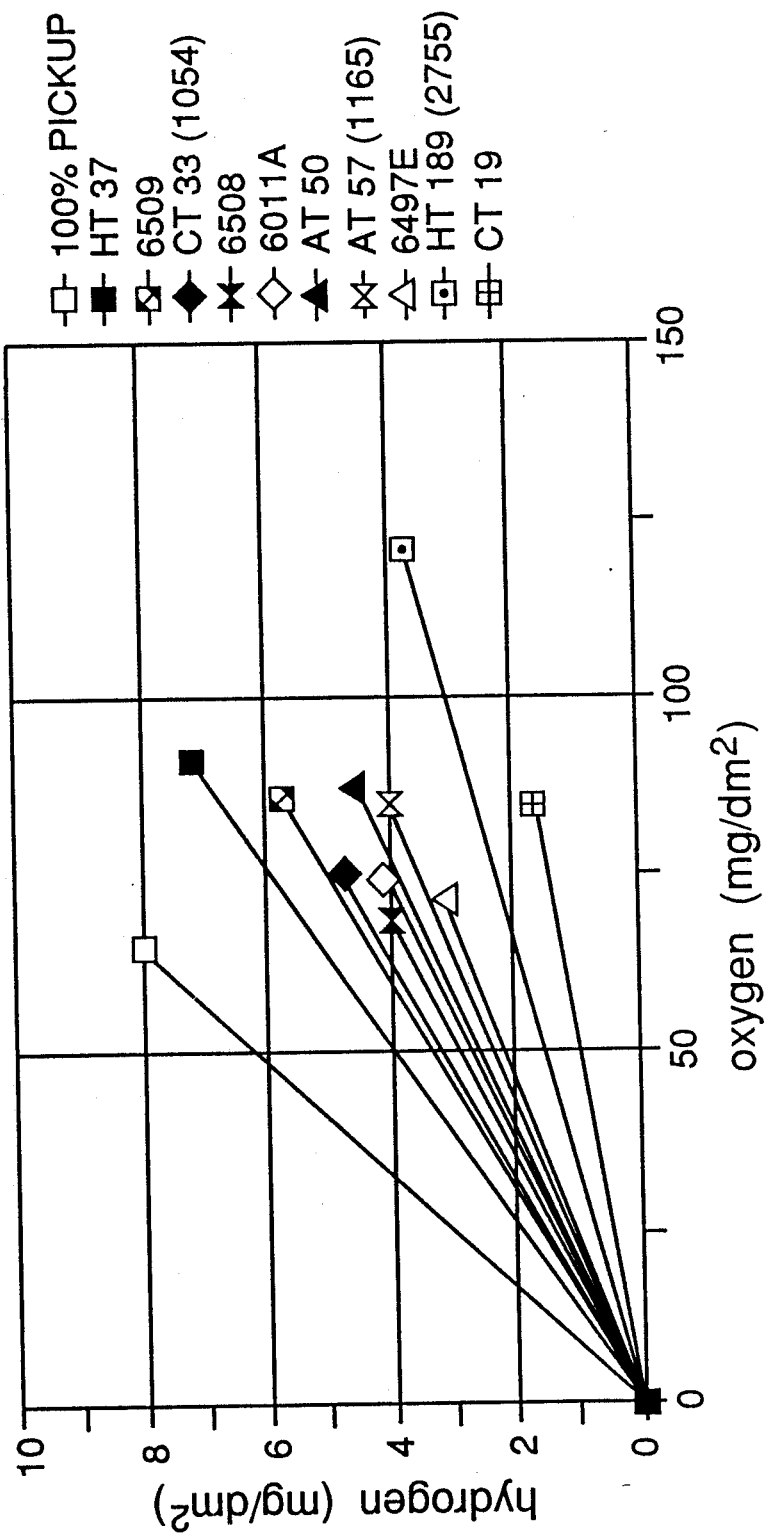
FIG. 1 is a graph showing an example of hydrogen uptake vs. oxidation gain in a typical out-of-reactor test.

The method of this invention makes it possible to predict the in-reactor hydriding order-of-merit for a group of zirconium based materials using an out-of-reactor test. As used herein, "Order-of-merit" indicates a ranking of materials according to their measured hydriding efficiencies, where hydriding efficiency is the percentage of available corrosion hydrogen absorbed by a specimen.

The basic hydriding method consists of using an autoclave containing a concentrated aqueous LiOH solution at an elevated temperature, preferably of 280° to 316° C., to charge hydrogen into the specimens. This method is described generally in Mugratroyd et al., *J. Nucl. Mat.* 23:249–256 (1967); and Kass, S., *Corrosion and Hydrogen Pickup of Zircaloy in Concentrated Lithium Hydroxide Solutions*, WAPD-TM-656, Bettis Atomic Power Laboratory, Pittsburgh, Pa. (1967), which publications are incorporated herein by reference. The aqueous reaction $Zr + 2H_2O \rightarrow ZrO_2 + 2H_2$ provides a hydrogen source to hydride zirconium alloys. Satisfactory hydrogen concentrations are achievable in exposures of as few as 7 days, resulting from elevated corrosion rates in relatively concentrated, 0.3 to 1.0M, lithium hydroxide (LiOH) solutions.

EXAMPLE

A series of tests shows the usefulness of this method as a predictive tool. In these tests, zirconium alloy materials, tested and ranked by the method of the present invention, were compared to the ranking of samples of the same materials used in pressure tubes within the N reactor at Richland, Wash. U.S.A., where they were contacted with water and nuclear radiation for a period of years.

Materials Tested

Table I lists the principal materials used in the hydriding orders-of-merit tests.

[Johnson et al. (1967); Johnson (1987)]. These lots were never irradiated in the Hanford N Reactor at Richland, Wash., U.S.A. The hydriding order-of-merit for these lots in the ETR tests was CT19 < AT50 < HT37.

The second group of Zircaloy-2 materials was from another ETR G-7 loop corrosion test series. This series was conducted on specimens from three ingots of material referred to as Type K [Johnson et al. (1967)]. Each ingot was represented in-reactor by several lots. Lots 6497E and 6508 represented Ingot 1, lot 6509 represented Ingot 2, and lot 6011A represented Ingot 3. The in-reactor hydriding order-of-merit trends for these lots, while less well-defined than for the previous ETR corrosion series, was Ingot 1 < Ingot 2 < Ingot 3.

The third group of Zircaloy-2 materials was selected from tubes irradiated for various lengths of service in the Hanford N Reactor. The tube location number in N Reactor is shown in parentheses, after the tube number. The tubes selected were AT57 (1165), CT33 (1054), and HT189 (2755). These tubes had accumulated more than 3000 operating days and showed dramatically different hydriding behavior [Lanning et al.]. To date, lot HT189 (2755) has shown the lowest hydriding rate of all N Reactor tubes examined that have been irradiated for more than 3000 operating days (FIG. 1).

Due to the different irradiation conditions of these three groups of Zircaloy-2 materials, an assessment of a overall hydriding order-of-merit cannot be readily performed. Accordingly, these comparison tests concern correlation with order-of-merit behavior within each group.

For comparison, specimens from two other alloys with hydriding histories under irradiation were included in the out-of-reactor program: Zircaloy-4 and

TABLE I

Summary of Principal Zirconium Alloy Hydride Test Materials

| Material | Lot | Reactor Exposure | Reference | Archive Material |
|---|---|---|---|---|
| Zircaloy-2[a] | AT-50<br>CT-19<br>HT-37 | ETR[b] | Johnson et al. (1967), and Johnson (1987) | Machined mechanical property specimens |
| Zircaloy-2[c] (Type K) | 6497 (Ingot 1)<br>6508 (Ingot 1)<br>6509 (Ingot 2)<br>6011 (Ingot 3) | ETR | Johnson et al. (1967) | Rolled plate |
| Zircaloy-2[d] | AT57 (1165)[e]<br>CT33 (1054)<br>HT189 (2755) | N Reactor | Lanning, FIG. 3 | Tube archive sections |
| Zircaloy-4 | — | ATR[f]/ETR | Johnson (1969)[g] and Johnson et al. (1974)[h] | Coupons |
| Zr-2.5 Nb | — | ATR/ETC | Johnson (1969),[g] and Johnson et al. (1974)[h] | Coupons |

[a] Corrosion/mechanical property specimens machined from unirradiated N Reactor Zircaloy-2 pressure tubes; these tubes were not installed in N Reactor.
[b] ETR = Engineering Test Reactor.
[c] Corrosion/mechanical property specimens from Type K Ingots 1, 2, and 3; the 4-digit numbers are lot numbers.
[d] Materials from pressure tubes that had service in the N Reactor.
[e] 1165 etc. are tube location numbers that are usually referenced in the literature instead of the respective tube numbers (AT57, etc.); both identifiers will be noted herein for these tubes and for others that have been routinely identified solely by their tube location numbers.
[f] ATR = Advanced Test Reactor.
[g] Johnson, A. B. Jr., Applications-Related Phenomena for Zirconium and Its Alloys, ASTM STP 458, pp. 271–285 (1969)
[h] Johnson et al., Zirconium in Nuclear Applications, ASTM STP 551, pp. 495–513 (1974).

Three groups of Zircaloy-2 materials, each having a different irradiation experience, were used in the tests.

The first group of materials was from corrosion test series in the G-7 loop of the Engineering Test Reactor (ETR). This group comprised three lots of N Reactor pressure tube materials, AT-50, CT-19 and HT-37

Zr-2.5 Nb. Both alloys were represented by specimens exposed in the ETR G-7 loop test series, and also in the Advanced Test Reactor (ATR) 1D loop [Johnson (1969)]. The Zircaloy-4 material generally had lower hydriding rates than Zircaloy-2 specimens with the same reactor exposure. Consistently, Zr-2.5 Nb specimens had the lowest hydriding rates of the nine zirconium based materials included in the ETR G-7 loop test series [Johnson (1969)].

Archive material for all alloys/lots listed in Table I were used for out-of-reactor tests to investigate potential correlations with the in-reactor hydriding orders-of-merit. Other lots of N Reactor tubing materials were also included in the out-of-reactor tests.

Table II provides the ranges of fabrication temperatures and element concentrations for the Zircaloy-2 test materials.

TABLE II

Actual and Allowable Ranges for Extrusion Temperature and Concentration of Key Elements for Zircaloy-2 Test Materials.

| Variable | Units | Actual Minimum | Actual Maximum | Allowable Minimum | Allowable Maximum |
|---|---|---|---|---|---|
| Extrusion Temperature[a] | °C. | 718 | 888 | — | — |
| Tin | wt % | 1.36 | 1.67 | 1.20 | 1.70 |
| Iron | wt % | 0.097 | 0.155 | 0.07 | 0.20 |
| Chromium | wt % | 0.073 | 0.108 | 0.05 | 0.15 |
| Nickel | wt % | 0.032 | 0.061 | 0.03 | 0.08 |
| Silicon | ppm (by wt) | 12 | 240[b] | — | 250[b] |
| Carbon | ppm (by wt) | 75 | 390 | — | 500 |
| Oxygen | ppm (by wt) | 610 | 1390 | — | 1400 |
| Nitrogen | ppm (by wt) | 15 | 82[b] | — | 100[b] |
| Hydrogen | ppm (by wt) | 3 | 23 | — | 50[b] |
| Aluminum | ppm (by wt) | 23 | 59 | — | 75 |
| Uranium | ppm (by wt) | 0 | 14[b] | — | 5[b] |
| Copper | ppm (by wt) | 4 | 32 | — | 50 |
| Tungsten | ppm (by wt) | 10 | 40 | — | 50 |
| Titanium | ppm (by wt) | 10 | 30 | — | 50 |

[a]The Type K alloys were rolled from billets to a 10-cm plate starting at 910° C. and finishing at 788° C. The final roll was at 882° C.
[b]Exceeds current ASTM Standard Specification for Wrought Zirconium and Zirconium Alloy Seamless and Welded Tubes for Nuclear Service (B 353-77a).

Table III summarizes the conditions investigated in the nine development and demonstration autoclave tests.

TABLE III

| Test No. | Test Type | Test Conditions[a] |
|---|---|---|
| | Out-of-Reactor Test Parameters. | |
| 1 | Development | 1.0 M LiOH, 316° C., 7 d |
| 2 | Development | 0.3 M LiOH, 280° C., 7 d |
| 3 | Development | 0.3 M LiOH, 316° C., 7 d |
| 4 | Development | 0.3 M LiOH, 295° C., 7 d |
| 5 | Development | 0.5 M LiOH, 295° C., 7 d |
| 6 | Development | 0.5 M LiOH, 295° C., 35 d |
| 7 | Develpoment | 0.3 M LiOH, 295° C., 28 d 3 cycles to 150° C. |
| 8 | Development | 0.3 M LiOH, 316° C., 7 d 2 cycles to 150° C. |
| 9 | Demonstration | 0.3 M LiOH 295° C., 28 d |

[a]Two autoclaves were used. Their volumes were 16.5 and 6.5 L, respectively. Their refreshment rates were 1.0 and 0.5 L/h, respectively.

The zirconium alloy specimens were nominally 2.0 to 2.5 cm by 0.6 to 0.7 cm by 0.16 to 0.31 cm. Surface preparations consisting of combinations of polishing (400 grit), etching (3 percent hydrofluoric acid, 30 percent nitric acid for 3 min.) and prefilming (360° C. steam for 3 d.) were evaluated in Test 1. Because prefilming did not improve hydriding discrimination, and since the tubing surface roughness necessitated the polish and etch, the polish and etch preparation without prefilming was used for all subsequent tests.

Test Conditions

Two autoclaves were used in the test series. The autoclave body material was prefilmed Type 347 stainless steel. The preweighed specimens were suspended from Type 304 stainless steel racks that had been autoclaved prior to the hydriding test series.

The required amounts of anhydrous LiOH were weighed using an analytical balance. The LiOH powder was added to boiling deionized water and stirred to hasten dissolution. After the solution cooled to room temperature, additional deionized water was added to prepare known volume (or known LiOH normality). After the lithium hydroxide solution was poured into the autoclave, pure (99 percent) argon was bubbled through the solution for a minimum of one hour. The autoclave was then sealed and raised to the test temperature.

The argon purge step was deemed necessary to minimize or eliminate all traces of air (oxygen) from the autoclave system. This step, or an alternate which includes repetitive evacuation of the system and argon back filling, must be incorporated if meaningful and reproducible hydrogen pickup values are to be obtained. The presence of air (oxygen) in the test solution can significantly reduce the hydrogen pickup during corrosion exposure. Purging or evacuation is considered superior to autoclave venting where vapor phase carry-over of the LiOH can alter the solution chemistry. The tests were conducted on a feed-and-bleed basis (1 l/hr flow rates).

Upon completion of the predetermined test time, the autoclave heaters were turned off. The specimens were removed, dried, examined and weighed, and the thickness of the oxide layers measured. Vacuum extraction at 1100° C. was utilized to determine the hydrogen pickup for each specimen.

Eight method development tests (Table III) were performed to establish conditions that would adequately provide the correct order-of-merit with sufficient discrimination in hydriding rate within a reasonable test period. Because some archive materials were in short supply, not all of the materials were inserted in all development tests. The Zircaloy-4 and Zr-2.5 Nb materials were only used in demonstration Test 9.

The hydrogen levels in Test 1 were much higher than target levels established for the lowest hydrider, HT189 (2755), from in-reactor data (39 versus 1 to 10 mg/dm$^2$). Hydrogen concentrations were beyond saturation levels for the test conditions, and masked differences that might otherwise have occurred in the materials. Test 2 was designed to reduce hydrogen pickup to about 1/50th of the Test 1 concentrations. While the correct order-of-merit was achieved in Test 2, hydrogen pickup was below this target level and not significantly above the base levels present in the materials. Tests 3 to 5 were designed to add 50 to 100 ppm to the materials and to investigate discrimination in hydrogen absorption efficiencies among the test materials. Of these three tests, only Test 3 achieved the target hydrogen concentrations. However, the three tests demonstrated that discrimination improved as the rate of oxidation and hydriding decreased.

Tests 6 to 8, then, were designed to evaluate the effects of low charging rate (Tests 4 and 5 conditions) on discrimination and the effects of increased test duration and thermal cycling on target hydrogen concentration. Rates of total weight gain (which, due to the small amount of hydrogen pickup, will hereafter be termed "oxidation rates") of 1.5 to 14.5 mg/dm$^2$ per day (mdd), for HT189 (2755), provided correct orders-of-merit. Oxidation rates below about 6 mdd provided the best discrimination. Oxidation rates that cause a gain above about 15 mdd may produce inconsistent results. When operating at the above oxidation rates, neither test temperature nor LiOH concentration appeared to be controlling order-of-merit. The two tests conducted with thermal cycling (Tests 7 and 8) did not show improved discrimination in hydrogen pickup compared to isothermal conditions. After evaluating these results, the Test 4 conditions were chosen for the demonstration test, but were extended to 28 d.

Test 9, the demonstration test, included materials from archive sections of seventeen N Reactor tubes that were statistically selected to evaluate the effect on hydrogen pickup of variations in trace element concentration and fabrication temperature. Lots from the N Reactor tube materials and Type K materials tested in the development tests were included in Test 9. Specimens of Zircaloy-4 and Zr-2.5 Nb were also included.

RESULTS

Results are presented in a tabular format containing the average hydrogen pickup (in ppm and absorption efficiency (percent)) and expected order-of-merit of each lot based on in-reactor performance (where an ordinal of 1 represents a lower hydrider than 2, etc.). Absorption efficiency represents the fraction of the hydrogen generated in the oxidation reaction that is absorbed by the specimen. Table IV presents these data from Test 7 for the three Zircaloy-2 groups appearing in Table I; these are graphically represented in FIG. 1.

TABLE IV

Summary Results for Test 7 (Zircaloy-2).

| Test Conditions | Lot | Hydrogen Pickup ppm | Absorption Efficiency, % | Expected Order of Merit[a] A | B | C |
|---|---|---|---|---|---|---|
| 0.3 M LiOH, 295° C., 28 d, 3 cycles to 150° C. | CT19 | 44 | 15 | — | — | 1 |
| | HT189 (2755) | 110 | 24 | 1 | — | — |
| | 6497E (Ingot 1)[b] | 65 | 34 | — | 1 | — |
| | AT57 (1165) | 123 | 38 | 2 | — | — |
| | AT50 | 100 | 41 | — | — | 2 |
| | 6011A (Ingot 3) | 81 | 43 | — | 3 | — |
| | 6508 (Ingot 1) | 86 | 45 | — | 1 | — |
| | CT33 (1054) | 150 | 51 | 3 | — | — |
| | 6509 (Ingot 2) | 120 | 54 | — | 2 | — |
| | HT37 | 152 | 63 | — | — | 3 |

[a]Expected Order-of-Merit is based on the relative hydriding behavior of the test materials under irradiation. Ordinals indicate the in-reactor order of hydriding (1 < 2 < 3). Group A compares N Reactor tubes examined after reactor service, group B compares Type K Zircaloy-2 exposed in the ETR, and group C compares three Zircaloy-2 lots from N Reactor tubes AT50, CT19, and HT37, exposed in the ETR.
[b]Both lots 6497E and 6508 are from Ingot 1, but with variations in metallurgical condition.

The results of Test 7 are representative of results observed in the seven development tests that had low oxidation rates. In the Expected Order-of-Merit column, the three Zircaloy-2 lots shown are represented by their own orders-of-merits. The results show that the N Reactor lots that were irradiated in the N Reactor (designated A) exhibit the same order-of-merit as observed in-reactor. The N Reactor lots that were irradiated in the ETR (designated C) also exhibit the same order-of-merit as observed in-reactor. These results are representative of all the low-oxidation rate tests.

Type K materials (designated B), however, showed inconsistent order-of-merit behavior in the development tests. In six of the seven low charging rat tests in which only lot 6497E represented Ingot 1 and in which Ingot 2 lot was not represented, the order-of-merit was the same as in-reactor (Ingot 1 < Ingot 3). However, in Test 7, when Ingot 1 was represented by lot 6508, then the order-of-merit was Ingot 1 > Ingot 3 (instead of 1 < 3). Moreover, when Ingot 2 (6509) is also considered, then, depending on whether Ingot 1 was represented by lot 6497E or 6508, the order-of-merit is Ingot 1 (6497E) < Ingot 3 < Ingot 2 or Ingot 3 < Ingot 1 (6508) < Ingot 2 (instead of 1 < 2 < 3).

Table V presents the hydriding characteristics for the materials in Test 9, the demonstration test.

TABLE V

Summary Results for Test 9 (Zircaloy-2, Zircaloy-4, and Zr-2.5 Nb)

| Test Conditions | Lot | Hydrogen Pickup ppm | Absorption Efficiency, % | Expected Order of Merit[a] A | B | C |
|---|---|---|---|---|---|---|
| 0.3 M, LiOH 295° C., 28 d | Zr-2.5 Nb | 62 | 5 | — | — | 1 |
| | CT20 (0758) | 50 | 15 | — | — | — |
| | HT186 | 76 | 18 | — | — | — |
| | HT685 | 89 | 19 | — | — | — |
| | Zircaloy-4 | 160 | 24 | — | — | 2 |
| | HT189 (2755) | 109 | 25 | 1 | — | — |
| | AT33 | 100 | 27 | — | — | — |
| | CT58 | 124 | 30 | — | — | — |
| | HT151 | 137 | 30 | — | — | — |
| | 6497E (Ingot 1) | 61 | 31 | — | 1 | — |
| | AT46 | 108 | 33 | — | — | — |
| | HT601 | 157 | 34 | — | — | — |
| | HT252 | 194 | 37 | — | — | — |
| | HT184 | 182 | 37 | — | — | — |
| | 6011A (Ingot 3) | 76 | 40 | — | 2 | — |
| | HT227 | 204 | 41 | — | — | — |
| | AT22 | 161 | 44 | — | — | — |
| | CT33 (1054) | 145 | 45 | 2 | — | — |
| | HT300 | 141 | 47 | — | — | — |
| | CT63 | 187 | 47 | — | — | — |
| | HT4 | 154 | 48 | — | — | — |

TABLE V-continued

Summary Results for Test 9 (Zircaloy-2, Zircaloy-4, and Zr-2.5 Nb)

| Test Conditions | Lot | Hydrogen Pickup ppm | Absorption Efficiency, % | Expected Order of Merit[a] A | B | C |
|---|---|---|---|---|---|---|
| | AT9 | 218 | 51 | — | — | — |

[a]Expected Order-of-Merit is based on the relative hydriding behavior of the test materials under irradiation. Ordinals indicate the in-reactor order of hydriding (1 < 2 < 3). Group A compares N Reactor tubes examined after reactor service; group B compares Type K Zircaloy-2 exposed in the Engineering Test Reactor (ETR), and group C compares ETR/ATR irradiations of Zircaloy-4 and Zr-2.5 Nb specimens.

In Test 9, data are presented for archive samples from five groups of materials: (1) N Reactor lots that were irradiated in the N Reactor (designated A in the order-of-merit column); (2) Type K lots that were irradiated in the ETR (designated B); (3) Zircaloy-4 and Zr-2.5 Nb lots that were irradiated in the ETR and ATR (designated C); (4) a single lot of CT20 (0758), an N Reactor material that was irradiated to low exposure in the N Reactor and which had been tested in one of the development tests; and (5) lots of N Reactor materials that were statistically selected from available archives to cover the range of element concentrations and fabrication temperatures within the N Reactor lots.

Several important observations can be made from these data. First, tubes HT189 (2755) and CT33 (1054) had the same order-of-merit observed in-reactor. Second, the two Type K materials (6011A and 6497E) had the same order-of-merit observed in-reactor. Third, the Zircaloy-4 and Zr-2.5 Nb materials have the same order-of-merit observed in-reactor and the Zr-2.5 Nb material had the lowest hydriding rate of all the materials tested in the autoclave, paralleling a large body of in-reactor experience. Fourth, the N Reactor tube materials show wide differences in hydriding rate. In fact, three N Reactor tube materials had lower hydriding absorption efficiencies that HT 189 (2755), the N Reactor lot that had previously shown the lowest in-reactor hydriding. Fifth, the hydriding resistance of Zircaloy-4 was exceeded by the hydriding resistance of three N Reactor Zircaloy-2 tube materials.

To summarize the results of all nine autoclave tests:

1. In the eight autoclave tests in which the oxidation rate was <14.5 mdd, the in-reactor order-of-merit was reproduced for the three principal N Reactor Zircaloy-2 materials [AT57 (1165), CT33 (1054), and HT189 (2755)].

2. In the two autoclave tests that included Lots AT50, CT19, and HT37, the lots had the same hydriding order as they had in-reactor.

3. In the eight autoclave tests having the low oxidation rates that included Ingots 1 and 3 of the Type K Zircaloy-2, six tests had the lots in the same order as in-reactor (1<3); in two tests, the hydriding order was reversed. In the one autoclave test containing Ingot 2, the in-reactor order was not obtained.

4. In the autoclave test that included Zircaloy-4, the material had a relatively low hydriding rate (as it had in-reactor); however, three N Reactor Zircaloy-2 tube materials had lower hydriding rates than Zircaloy-4 in this test.

5. In the one autoclave test that included Zr-2.5 Nb, the material had the lowest hydriding rate of any material tested, consistent with in-reactor results.

6. Test 9 demonstrated that, even within a given set of N Reactor specifications for composition and fabrication parameters (Table II), large lot-to-lot variations in hydriding behavior can be expected; more than a factor of three was observed between lots CT20 and AT9.

CONCLUSIONS

This test series demonstrated an out-of-reactor test that reproduces in-reactor hydriding trends for zirconium-based materials. With only minor exceptions associated with the Type K materials (which had exhibited less clearcut in-reactor order-of-merit performance than the other Zircaloy alloys), the autoclave runs conducted at relevant oxidation rates (1.5 to 14.5 mdd) provided correlations between in-reactor and out-of-reactor hydriding orders-of-merit for the test materials.

Having illustrated and described the principles of our invention with reference to one preferred embodiment, it should be apparent to those persons skilled in the art that such invention may be modified in arrangement and detail without departing from such principles. We claim as our invention all such modifications as come within the true spirit and scope of the following claims.

We claim:

1. A process for determining which of at least two zirconium materials having different composition and/or fabrication has the greatest resistance to hydriding in an environment of a water cooled nuclear fission reactor, the process comprising:

contacting under the same conditions, samples of said zirconium alloy materials with an aqueous LiOH solution at an elevated temperature to cause the zirconium alloy samples to gain weight at a rate of not more than about 15 mg/dm$^2$/day for as long as necessary to obtain a measurable weight gain;

determining the ratio of hydrogen weight gain to oxygen weight gain for each sample; and then comparing ratios, the material having the lowest ratio being the material which will experience the least amount of hydriding in an environment of a water cooled nuclear fission reactor.

2. The process of claim 1 wherein the contacting is performed at conditions which cause the samples to gain at least about 1.5 mg/dm$^2$/day.

3. The process of claim 2 wherein the contacting is conducted for a period of at least seven days.

4. The process of claim 1 wherein the contacting is performed at conditions which cause the samples to gain less than about 6 mg/dm$^2$/day.

5. The process of claim 1 wherein the LiOH concentration is 0.3 to 1.0M.

6. The process of claim 1 wherein the temperature is 280° to 316° C.

7. A process for determining which of at least two zirconium alloy materials having different composition and/or fabrication will hydride least rapidly in the presence of water and a source of nuclear radiation, the process comprising:

contacting, under the same conditions, samples of said zirconium alloy materials with an 0.3 to 1.0M aqueous LiOH solution at a temperature of 280° to 316° C. to cause the zirconium alloy to gain weight at a rate of 1.5 to 15 mg/dm$^2$/day for a period of at least seven days;

determining the ratio of hydrogen weight gain to oxygen weight gain for each sample; an then comparing the ratios, the material having the lowest ratio being the material which will experience the least amount of hydriding in the presence of water and nuclear radiation.

* * * * *